United States Patent
Haziza

(10) Patent No.: US 11,026,735 B2
(45) Date of Patent: Jun. 8, 2021

(54) BONE MARROW ASPIRATION ADAPTOR ASSEMBLY

(71) Applicant: Premia Spine Ltd., Ramat Poleg (IL)

(72) Inventor: Rafi Haziza, Kiryat Bialik (IL)

(73) Assignee: Premia Spine Ltd., Ramat Poleg (IL)

( * ) Notice: Subject to any disclaimer, the term of this patent is extended or adjusted under 35 U.S.C. 154(b) by 113 days.

(21) Appl. No.: 15/907,295

(22) Filed: Feb. 28, 2018

(65) Prior Publication Data

US 2019/0262055 A1 Aug. 29, 2019

(51) Int. Cl.
| | | |
|---|---|---|
| *A61B 17/88* | (2006.01) | |
| *A61B 17/70* | (2006.01) | |
| *A61B 17/00* | (2006.01) | |
| *A61B 17/86* | (2006.01) | |
| *A61F 2/28* | (2006.01) | |

(52) U.S. Cl.
CPC ...... *A61B 17/8875* (2013.01); *A61B 17/7082* (2013.01); *A61B 17/8897* (2013.01); *A61B 17/864* (2013.01); *A61B 2017/00477* (2013.01); *A61B 2217/005* (2013.01); *A61F 2002/2835* (2013.01)

(58) Field of Classification Search
CPC ............ A61B 17/7082; A61B 17/1635; A61B 17/8875; A61B 10/025; A61B 17/8897
USPC .................................................. 606/104, 304
See application file for complete search history.

(56) References Cited

U.S. PATENT DOCUMENTS

| | | | | |
|---|---|---|---|---|
| 7,011,621 | B2 * | 3/2006 | Sayet | .................... A61F 2/0036 600/30 |
| 2006/0111761 | A1 | 5/2006 | Olson | |
| 2009/0264895 | A1 * | 10/2009 | Gasperut | ............ A61B 17/7098 606/104 |
| 2010/0030105 | A1 * | 2/2010 | Noishiki | ............... A61B 10/025 600/567 |
| 2010/0298887 | A1 | 11/2010 | Jordan | |
| 2011/0112436 | A1 | 5/2011 | Jones | |
| 2012/0197311 | A1 * | 8/2012 | Kirschman | ........ A61B 17/7098 606/304 |
| 2014/0194886 | A1 * | 7/2014 | Poulos | ................. A61B 17/864 606/94 |

OTHER PUBLICATIONS

PCT Written Opinion and Search Report PCT/IB2019/051541, dated Jul. 1, 2019.

* cited by examiner

*Primary Examiner* — Si Ming Ku

(74) *Attorney, Agent, or Firm* — Dekel Patent Ltd.; David Klein

(57) ABSTRACT

An assembly includes a bone marrow aspiration adaptor (10), which includes a distal interface member (12) and a proximal interface member (14), which extend in opposite directions from a body (16). A lumen (18) extends through the distal interface member (12) and the proximal interface member (14). The proximal interface member (14) includes a fluid connector (22). A seal (24) is disposed in the distal interface member (12) inside the lumen (18).

8 Claims, 3 Drawing Sheets

BONE MARROW ASPIRATION ADAPTOR ASSEMBLY

FIELD OF THE INVENTION

The present invention relates generally to methods and apparatus for bone marrow aspiration during spinal surgery.

BACKGROUND OF THE INVENTION

Spinal arthrodesis (spinal fixation) is the indicated treatment for, among others, conditions of translational instability (spondylolisthesis, degenerative spondylolisthesis, and fracture), conditions of axial instability (tumor, fracture, degenerative disease), conditions of mechanical pain (pseudarthrosis, discogenic back pain, and adjacent level instability), and conditions of deformity (scoliosis, degenerative scoliosis, flat-back syndrome, and spondyloarthropathies).

Pedicle screw fixation is often used to perform spinal arthrodesis. The pedicle is the strongest portion of the vertebrae, transmitting all forces from the posterior elements to the vertebral body. It can withstand stresses of rotation, side bending, and extension of the spine, and is an ideal structure to lock into and control with posterior instrumentation when spinal fixation is needed.

In an effort to maximize surgical success, it is common to harvest bone graft, such as bone marrow, at the surgical site and use the bone graft to improve the fusion. However, the harvesting of autograft bone from the patient is associated with a considerable complication rate and may prove to be a source of chronic pain in many patients.

SUMMARY OF THE INVENTION

The present invention seeks to provide an improved device for bone marrow aspiration during spinal surgery, as described more in detail hereinbelow. The term "bone marrow" includes any kind of cell which is harvested from the patient's bone.

The invention enables transpedicular aspiration of marrow cells, such as including osteoprogenitor cells used in spine fusion augmentation. The device of the invention adapts to and mounts on the same instrumentation for insertion of K-wires and installation of pedicle screws and other spinal surgical tools and devices, without having to remove the existing instrumentation. Thus, the invention enables significantly safer and quicker graft harvesting, while significantly reducing or eliminating the risks of complications and morbidity.

There is thus provided in accordance with an embodiment of the present invention an assembly including a bone marrow aspiration adaptor including a distal interface member and a proximal interface member, which extend in opposite directions from a body, wherein a lumen extends through the distal interface member and the proximal interface member, the proximal interface member including a fluid connector, and a seal disposed in the distal interface member inside the lumen. The lumen may be formed with a shoulder.

The bone marrow aspiration adaptor may be coupled to a surgical tool assembly, wherein a shaft of the surgical tool assembly is received in the lumen and sealed by the seal.

The surgical tool assembly may be formed with a lumen. The surgical tool assembly may include a cannulated screwdriver or a cannulated pedicle probe.

A proximal end of the shaft of the surgical tool assembly may abut against the shoulder.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1A:
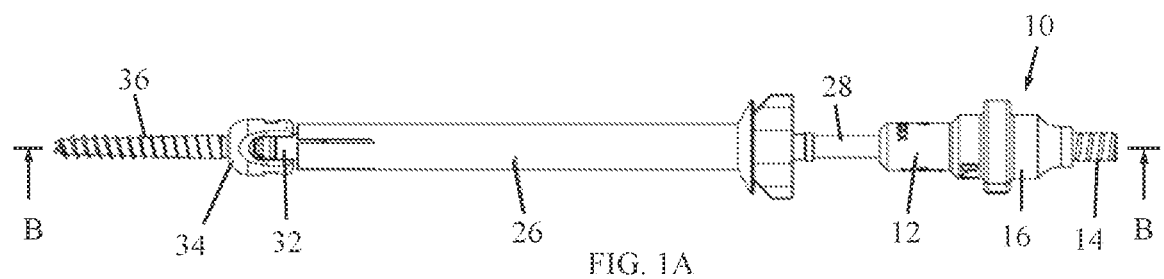
FIGS. 1A, 1B and 1C are simplified front-view, sectional and exploded perspective views, respectively, of a surgical tool assembly with a bone marrow aspiration adaptor, constructed and operative in accordance with an embodiment of the present invention, wherein the view of FIG. 1B is taken along lines B-B in FIG. 1A.
Figure 1B:
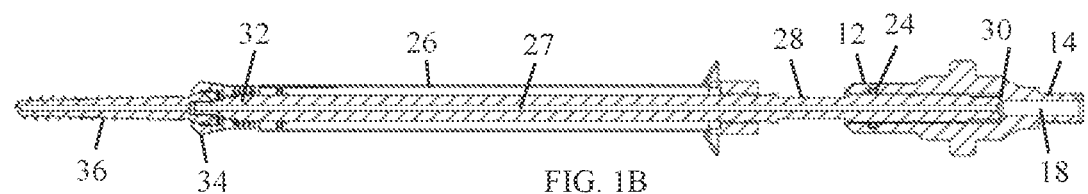
Figure 1C:
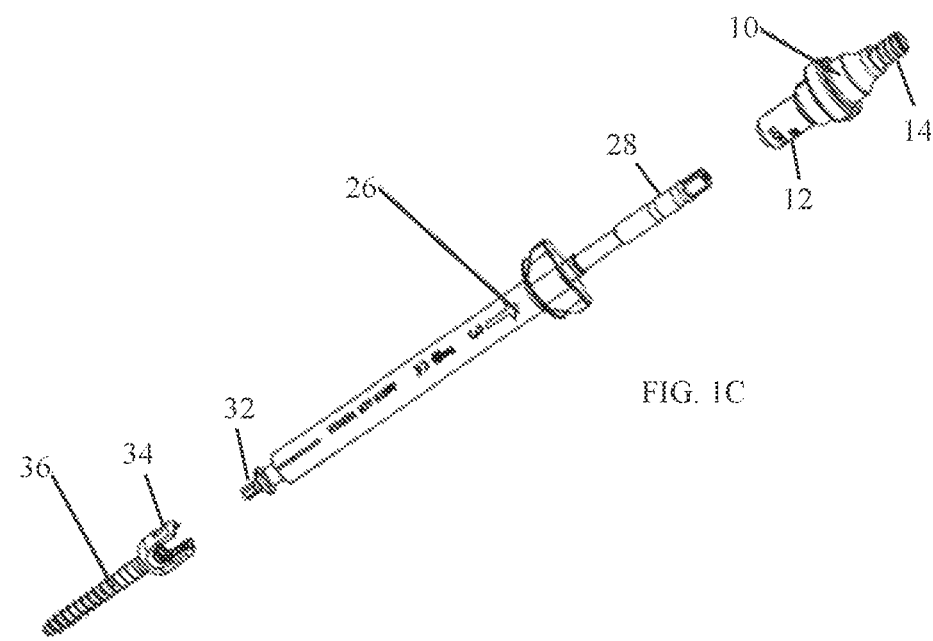

Reference is now made to FIGS. 1A, 1B and 1C, which illustrate a surgical tool assembly with a bone marrow aspiration adaptor 10, constructed and operative in accordance with an embodiment of the present invention. The bone marrow aspiration adaptor 10 is shown by itself in FIGS. 2A and 2B, to which reference is also made.

Figure 2A:
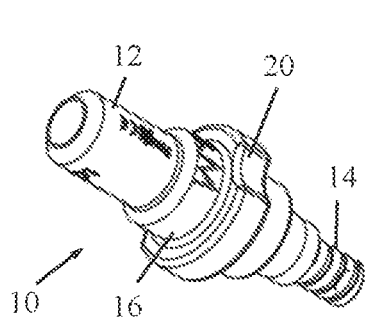
FIGS. 2A and 2B are simplified pictorial and partially cutaway-view illustrations, respectively, of the bone marrow aspiration adaptor.
Figure 2B:
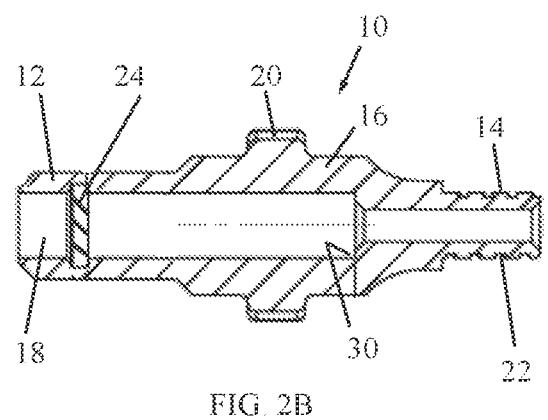

As seen best in FIGS. 2A-2B, the bone marrow aspiration adaptor 10 includes a distal interface member 12 and a proximal interface member 14, which extend in opposite directions from a body 16. A lumen 18 extends through distal interface member 12 and proximal interface member 14. Body 16 may include a grasping portion 20, which may be formed with recesses for grasping with fingers.

The distal interface member 12 may have a smooth outer contour, as shown in the non-limiting illustrated embodiment, but alternatively, may be formed with threads or other connecting structure. The proximal interface member 14 may include a fluid connector 22 for connection with a suction source (not shown) for aspiration of material, such as bone marrow, blood or other substances, through lumen 18. The distal interface member 12 may include a seal 24 (e.g., an O-ring) inside lumen 18. Seal 24 is important because it allows easy and quick coupling of the bone marrow aspiration adaptor 10 to the existing surgical instrumentation while at the same time ensuring that the material being aspirated does not leak out.

The bone marrow aspiration adaptor 10 may be constructed of any suitable, medically safe material, such as but not limited to, stainless steel, titanium alloy and others.

As seen in FIGS. 1A-1C, the bone marrow aspiration adaptor 10 may be coupled to surgical tool assembly, which may include a cannulated surgical tool 26, such as a cannulated screwdriver 26 formed with a lumen 27. Screwdriver 26 may include a proximal (hollow) shaft 28 which can be inserted into lumen 18 of bone marrow aspiration adaptor 10. As seen in FIG. 1B, seal 24 fluidly seals the connection of shaft 28 in lumen 18. The proximal end of shaft 28 may abut against a shoulder 30 (FIG. 2B) formed in a proximal portion of lumen 18. This provides the surgeon with a positive stop which can be felt, thus providing an indication of proper insertion of the shaft 28. The distal end of cannulated screwdriver 26 may include a screw connecting member 32, which couples with a head 34 (e.g., polyaxial head) of a pedicle screw 36.

Figure 3A:
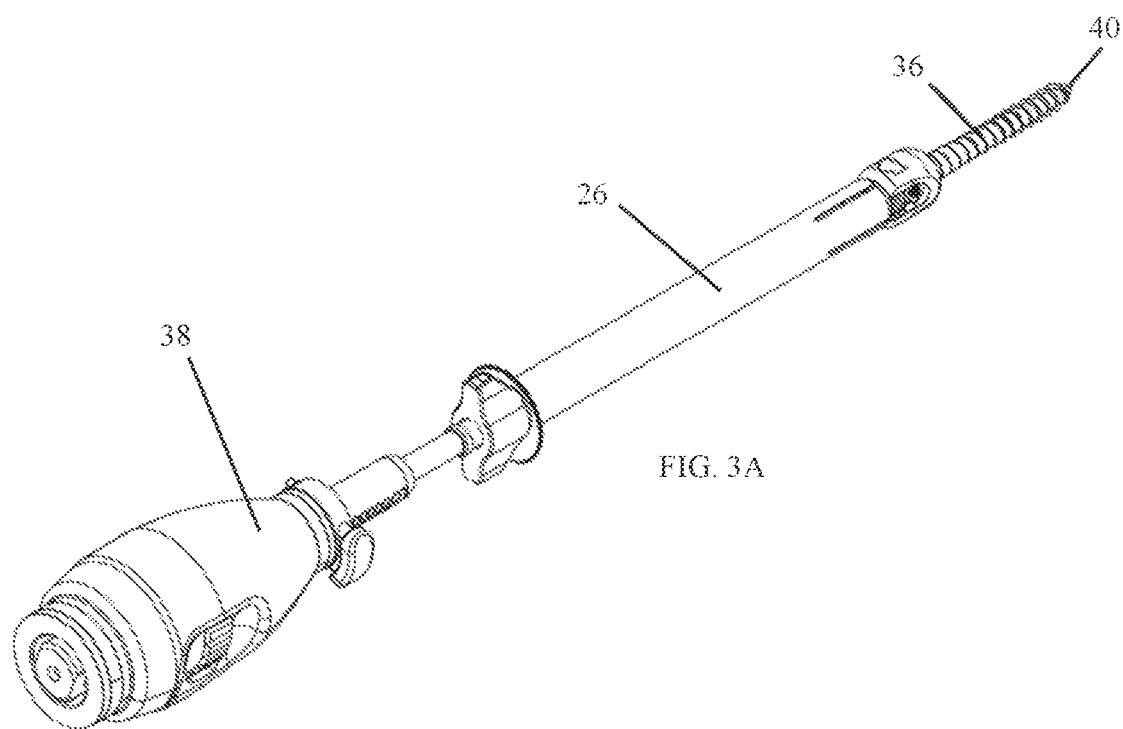
FIGS. 3A and 3B are simplified pictorial and exploded illustrations, respectively, of the same surgical tool assembly of FIGS. 1A-1C, without the bone marrow aspiration adaptor and used with a K-wire adaptor.
Figure 3B:
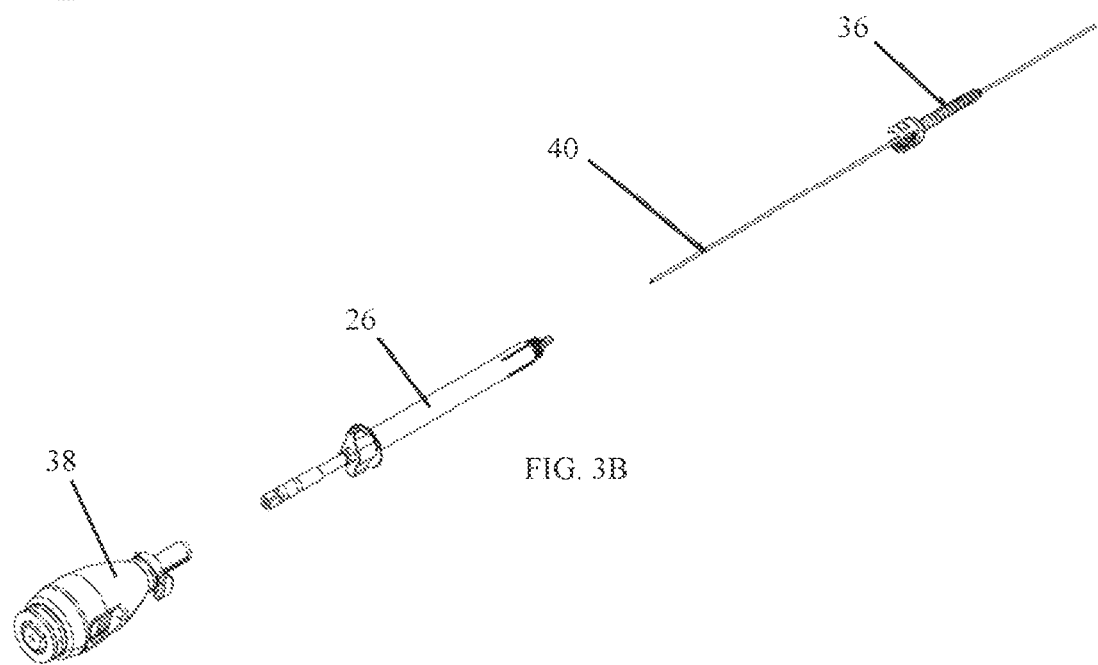

Reference is now made to FIGS. 3A and 3B, which illustrate the same surgical tool assembly of FIGS. 1A-1C, but without the bone marrow aspiration adaptor and instead used with a K-wire adaptor 38.

The illustrated K-wire adaptor 38 is described in PCT Patent Application PCT/IB2016/052074, but the invention is not limited to this type of adaptor. In brief, the K-wire adaptor 38 enables inserting a K-wire 40 through the lumen of cannulated surgical tool 26. As seen in FIGS. 3A and 3B, the K-wire 40 also passes through the lumen of the screw 36. The K-wire adaptor 38 has one or more knobs to position the K-wire 40 so it protrudes (e.g., a few mm) beyond the distal tip of the screw 36 (or the tip of some other surgical tool). The K-wire adaptor 38 is then used to lock the K-wire 40 with respect to the screw 36 or tool. The K-wire adaptor 38 is adjustable so that its proximal end can be flush with the proximal end of the K-wire 40, so that the surgeon can hammer or otherwise apply force on the proximal end of K-wire adaptor 38 in order to advance the K-wire 40 and screw 36 or tool together. The K-wire 40 breaches the cortical bone (or other spinal structure which the surgeon wishes to breach) and brings the tip of the cannulated screw 36 or tool to the bone surface. From there, the surgeon can screw in the pedicle screw 36 or advance the tool without concern for slipping. Without the device, the screw or tool can slip at the point of entry. The tip of the K-wire also ensures that the entry point is not lost during screw angulation, and facilitates finding or changing entry points.

A significant advantage of the assembly of the invention is that the surgeon can simply detach K-wire adaptor 38 from cannulated surgical tool 26 and replace it with the bone marrow aspiration adaptor 10, which couples with cannulated surgical tool 26, as described above with reference to FIGS. 1A-1C. The cannulated surgical tool 26 remains in place with the screw 36, and the material is aspirated (sucked by a suction device) through the lumens of the screw 36 and surgical tool (e.g., screwdriver) 26 through the lumen 18 of bone marrow aspiration adaptor 10, and eventually collected for use (such as in the same surgical procedure or later use).

Figure 4A:
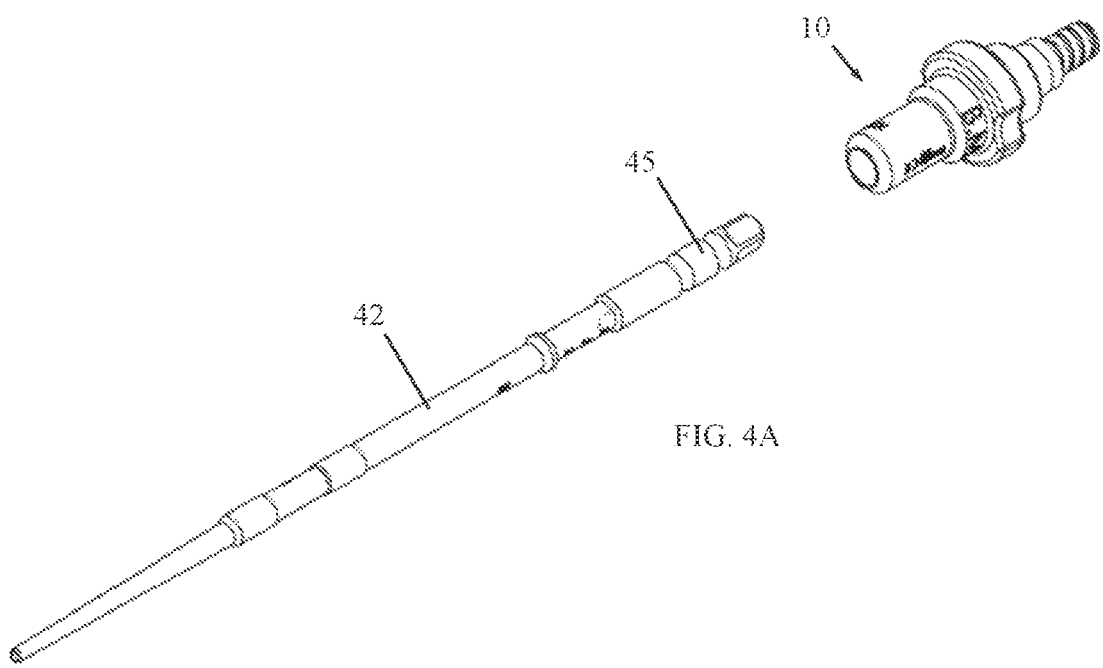
FIGS. 4A, 4B and 4C are simplified exploded perspective, front-view and sectional views, respectively, of another surgical tool assembly with a bone marrow aspiration adaptor, constructed and operative in accordance with an embodiment of the present invention, wherein the view of FIG. 4C is taken along lines C-C in FIG. 4B.
Figure 4B:
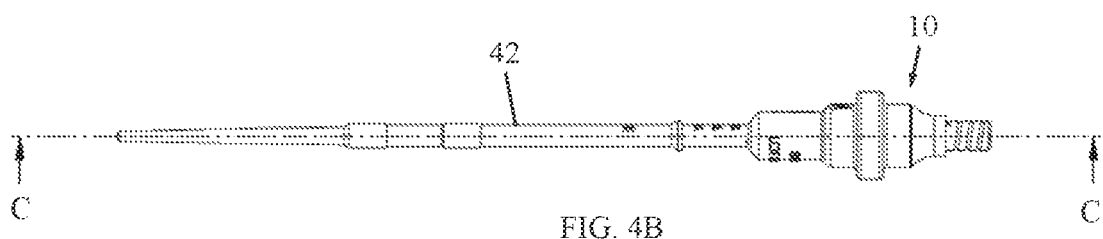
Figure 4C:
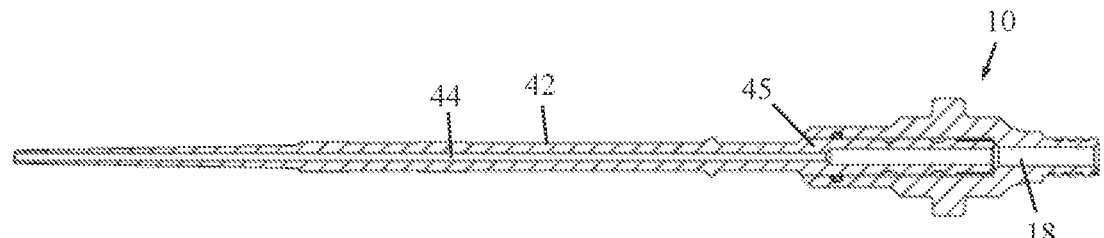

Reference is now made to FIGS. 4A, 4B and 4C, which illustrate another surgical tool assembly with bone marrow aspiration adaptor 10, constructed and operative in accordance with an embodiment of the present invention. In this tool assembly, bone marrow aspiration adaptor 10 is fitted on a cannulated pedicle probe 42, which is formed with a lumen 44 (FIG. 4C). A shaft 45 of cannulated pedicle probe 42 is inserted in lumen 18 of bone marrow aspiration adaptor 10 as described above.

Figure 5:
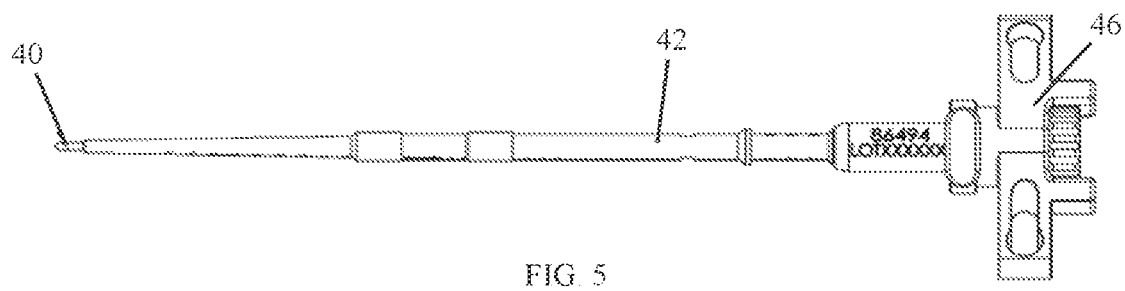
FIG. 5 is a simplified front-view illustration of the same surgical tool assembly of FIGS. 4A-4C, without the bone marrow aspiration adaptor and used with a K-wire handle.

Reference is now made to FIG. 5, which illustrates the same surgical tool assembly of FIGS. 4A-4C, without the bone marrow aspiration adaptor and used with a K-wire handle 46. The K-wire handle 46 can manipulate a K-wire 40 that passes through the lumen of cannulated pedicle probe 42. Once again, a significant advantage of the assembly of the invention is that the surgeon can simply detach K-wire handle 46 from cannulated pedicle probe 42 and replace it with the bone marrow aspiration adaptor 10 for aspiration of bone marrow.

What is claimed is:

1. An assembly comprising:
    a surgical tool adaptor comprising a distal interface member and a proximal interface member, which extend in opposite directions from a body, wherein a lumen extends through said distal interface member and said proximal interface member, said proximal interface member comprising a fluid connector; and
    a seal disposed in said distal interface member inside said lumen, and wherein said lumen has a proximal portion, which extends distally from a proximal end of said proximal interface member to a conical opening, a distal end of said conical opening being larger in diameter than said proximal portion of said lumen, and said lumen has a distal portion, which extends proximally from a distal end of said distal interface member to said distal end of said conical opening, said distal portion of said lumen being larger in diameter than said distal end of said conical opening so as to form a shoulder at a junction of said distal portion of said lumen and said distal end of said conical opening, and wherein said surgical tool adaptor is coupled to a surgical tool assembly that comprises a shaft that passes distally through said distal interface member and said shaft comprises a screw connecting member which is distal to said distal interface member.

2. The assembly according to claim 1, wherein a proximal end of said conical opening and said proximal portion of said lumen are equal in diameter.

3. The assembly according to claim 1, wherein said shaft is sealed by said seal.

4. The assembly according to claim 1, wherein said surgical tool assembly is formed with a lumen.

5. The assembly according to claim 1, wherein said shaft is part of a cannulated screwdriver.

6. The assembly according to claim 1, wherein said screw connecting member couples with a head of a pedicle screw.

7. The assembly according to claim 1, wherein a proximal end of said shaft abuts against said shoulder.

8. A method of bone marrow aspiration comprising using the assembly of claim 1 to aspirate bone marrow through said lumen of said surgical tool adaptor.

* * * * *